United States Patent
Guttuso, Jr.

(10) Patent No.: US 6,310,098 B1
(45) Date of Patent: Oct. 30, 2001

(54) METHOD OF TREATING SYMPTOMS OF HORMONAL VARIATION, INCLUDING HOT FLASHES

(75) Inventor: Thomas J. Guttuso, Jr., Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 09/620,979

(22) Filed: Jul. 21, 2000

Related U.S. Application Data

(60) Provisional application No. 60/145,061, filed on Jul. 22, 1999.

(51) Int. Cl.⁷ .................................................. A61K 31/195
(52) U.S. Cl. ............................................................ 514/567
(58) Field of Search ............................................. 514/567

(56) References Cited

U.S. PATENT DOCUMENTS

| | | |
|---|---|---|
| 4,960,931 | 10/1990 | Butler et al. . |
| 5,719,185 | 2/1998 | Bountra e tl. . |
| 5,847,151 | 12/1998 | Silverman et al. . |
| 5,962,505 | 10/1999 | Bobrove et al. . |
| 6,020,370 | 2/2000 | Horwell et al. . |
| 6,028,214 | 2/2000 | Silverman et al. . |

FOREIGN PATENT DOCUMENTS

| | | |
|---|---|---|
| WO 98/58641 | 12/1998 | (WO) . |
| WO 99/08671 | 2/1999 | (WO) . |

OTHER PUBLICATIONS

Bryans et al., "3–Substituted GABA Analogs with Central System Activity: A Review," *Med. Res. Rev.* 19:149–177 (1999).

Bryans et al., "Identification of Novel Ligands for th Gabapentin Binding Site on the $\alpha_2\delta$ Subunit of a Calcium Channel and Their Evaluation as Anticonvulsant Agents," *J. Med. Chem.* 41:L1838–1845 (1998).

Gee et al., "The Novel Anticonvulsant Drug, Gabapentin (Neurontin), Binds to the $\alpha_2\delta$ of a Calcium Channel," *J. Biol. Chem.* 271(10):5768–5776 (1996).

Guttusso, "Gabapentin's Effects on Hot Flashes and Hypothermia," *Neurology* 54:2161–2163 (2000).

*Primary Examiner*—Raymond Henley, III
(74) *Attorney, Agent, or Firm*—Nixon Peabody LLP

(57) ABSTRACT

One aspect of the present invention relates to a method of treating hot flashes in a patient which is carried out by providing a compound which binds a $\alpha_2\delta$ subunit of a voltage-gated calcium channel and administering the compound to a patient experiencing hot flashes under conditions effective to treat the hot flashes. Another aspect of the present invention relates to a method for treating a symptom of hormonal variation in a patient which is carried out by providing a compound which binds a $\alpha_2\delta$ subunit of a voltage-gated calcium channel and administering the compound to a patient experiencing a symptom of hormonal variation under conditions effective to treat the symptom of hormonal variation. Further aspects of the present invention relate to the administration of a compound which binds a $\alpha_2\delta$ subunit of a voltage-gated calcium channel as an anti-pyretic agent (for treating fever) or as an anti-emetic agent (for treating nausea and emesis).

36 Claims, No Drawings

METHOD OF TREATING SYMPTOMS OF HORMONAL VARIATION, INCLUDING HOT FLASHES

This application claims priority benefit of U.S. Provisional Patent application Ser. No. 60/145,061, filed Jul. 22, 1999, which is hereby incorporated by reference.

FIELD OF THE INVENTION

The present invention relates generally to methods of treating symptoms of hormonal variation, including hot flashes, treating fever, and treating nausea and emesis.

BACKGROUND OF THE INVENTION

Hot flashes or flushing occur commonly in menopausal women. This is characterized by a sudden onset of warmth in the face and neck and often progressing to the chest. Such an episode generally lasts several minutes and is evidenced by a visible flushing of the skin. Often such episodes are accompanied by sweating, dizziness, nausea, palpitations and diaphoresis. Such symptoms can disrupt sleep and interfere with the quality of life. Although the cause of hot flashes are not completely understood, they are thought to be a disorder of thermoregulation resulting from a transient lowering of the hypothalamic temperature regulatory set point (Kronenberg et al., "Thermoregulatory Physiology of Menopausal Hot Flashes: A Review," *Can. J. Physiol. Pharmacol.*, 65:1312–1324 (1987)). In post-menopausal woman, the cause of such hot flashes is believed to be a consequence of declining estrogen levels. Thus, it is not surprising that hot flashes also occur in a high percentage of women taking the anti-estrogen drug tamoxifen.

Men may also have hot flashes following androgen-deprivation therapy (from bilateral orchiectomy or treatment with a gonadotrophin-releasing-hormone agonist) for metastatic prostate cancer.

Although estrogen replacement therapy is the most direct and effective treatment for hot flashes in women, there are women in whom such therapy is contraindicated, i.e., women with breast cancer or a strong family history of breast cancer, a history of clotting, severe migraine, or who are averse to taking the drug.

In these women, there are alternative medications to prevent or treat the serious consequences of menopause, such as osteoporosis and raised serum lipid levels. Included in this category are the selective estrogen-receptor modulators (SERMs), such as raloxifene (see U.S. Pat. No. 5,534,526 to Cullinan), which selectively bind to and activate the estrogen receptors of some tissues such as bone, and block the receptors of others, i.e., breast and uterus. In so doing, they lack the negative impact that prolonged estrogen therapy may have on these organs. However, in contrast to estrogen, SERMs are not as effective in preventing hot flashes.

Other than estrogen-replacement therapy, there are no effective means to alleviate hot flashes. Low dose oral megestrol acetate, a progestational agent, was shown to reduce the frequency of hot flashes in both men and women in a short term study (Loprinzi et al., "Megestrol Acetate for the Prevention of Hot Flashes," *N. Engl. J. Med.* 331:347–351 (1994)). However, chronic adrenal insufficiency can be a side effect of low dose megestrol acetate when taken long term. Transdermal clonidine, a centrally active α-agonist, had only a moderate effect on the frequency and severity of hot flashes in tamoxifen-treated women (Goldberg et al., "Transdermal Clonidine for Ameliorating Tamoxifen-induced Hot Flashes," *J. Clin. Onc.* 12:155–158 (1994)).

Accordingly, there is a need for an alternative method of treating symptoms of hormonal variation, including hot flashes, which overcomes the deficiencies in the relevant art.

SUMMARY OF THE INVENTION

One aspect of the present invention relates to a method of treating hot flashes in a patient which is carried out by providing a compound which binds an $\alpha_2\delta$ subunit of a voltage-gated calcium channel and administering the compound to a patient experiencing hot flashes under conditions effective to treat the hot flashes.

Another aspect of the present invention relates to a method for treating a symptom of hormonal variation in a patient which is carried out by providing a compound which binds an $\alpha_2\delta$ subunit of a voltage-gated calcium channel and administering the compound to a patient experiencing a symptom of hormonal variation under conditions effective to treat the symptom of hormonal variation.

Yet another aspect of the present invention relates to a method of treating fever in a patient which is carried out by providing a compound which binds an $\alpha_2\delta$ subunit of a voltage-gated calcium channel and administering the compound to a patient experiencing a fever under conditions effective to treat the fever.

A further aspect of the present invention relates to a method of treating nausea and emesis in a patient which is carried out by providing a compound which binds an $\alpha_2\delta$ subunit of a voltage-gated calcium channel and administering the compound to a patient experiencing nausea and emesis under conditions effective to treat the nausea and emesis.

The present invention provides an improved treatment for symptoms of hormonal variation, including hot flashes, which can be significantly uncomfortable and seriously affect one's quality of life. Compounds which are active at the $\alpha_2\delta$ subunit of a voltage-gated calcium channel can be administered in a manner which is effective to reduce or substantially eliminate the occurrence or severity of hot flashes. In addition, the therapeutic use of such compounds as anti-pyretic and anti-emetic agents is also contemplated. According to preferred aspects of the present invention, two known compounds—gabapentin and pregabalin—can be administered to effect such treatments. Moreover, because gabapentin is well tolerated, its use according to the presently claimed invention is not believed to raise any new health concerns.

DETAILED DESCRIPTION OF THE INVENTION

One aspect of the present invention relates to a method of treating hot flashes in a patient which is carried out by providing a compound which binds an $\alpha_2\delta$ subunit of a voltage-gated calcium channel ("VGCC") and administering the compound to a patient experiencing hot flashes under conditions effective to treat the hot flashes.

Another aspect of the present invention relates to a method for treating a symptom of hormonal variation in a patient which is carried out by providing a compound which binds an $\alpha_2\delta$ subunit of a VGCC and administering the compound to a patient under conditions effective to treat the symptom of hormonal variations. A symptom of hormonal variation which is readily treated according to the present invention includes, but is not limited to, hot flashes.

Suitable compounds which are active at the $\alpha_2\delta$ subunit of VGCC include, without limitation, γ-aminobutyric acid ("GABA") analogs as well as pharmaceutically acceptable salts thereof. Suitable salts can be prepared according to known techniques.

GABA analogs are compounds which are derived from or based on GABA. GABA analogs are either readily available or readily synthesized using methodologies known to those of skill in the art. Exemplary GABA analogs and their salts have been described in U.S. Pat. No. 4,024,175 to Satzinger et al., U.S. Pat. No. 5,563,175 to Silverman et al., Bryans et al., "Identification of Novel Ligands for the Gabapentin Binding Site on the $\alpha_2\delta$ Subunit of a Calcium Channel and Their Evaluation as Anticonvulsant Agents," *J. Med. Chem.* 41:1838–1845 (1998), and Bryans et al., "3-Substituted GABA Analogs with Central Nervous System Activity: A Review," *Med. Res. Rev.* 19:149–177 (1999), which are hereby incorporated by reference. GABA analogs which are preferred for use according to the methods of the present invention include, without limitation, gabapentin and pregabalin.

Gabapentin, (1-aminomethyl)cyclohexaneacetic acid, is a GABA analog which has been used previously in the treatment of epilepsy, neurogenic pain, restless legs syndrome, essential tremor, bipolar disorder, and migraine (Magnus, "Nonepileptic Uses of Gabapentin," *Epilepsia*, 40:S66-S72 (1999), which is hereby incorporated by reference). Gabapentin has been shown to bind to a single site in the brain with high affinity, the $\alpha_2\delta$ subunit of VGCC (Bryans et al., "3-Substituted GABA Analogs with Central Nervous System Activity: A Review," *Med. Res. Rev.* 19:149–177 (1999), which is hereby incorporated by reference).

Pregabalin, (S)-(3-aminomethyl)-5-methylhexanoic acid or (S)-isobutyl GABA, is another GABA analog whose use as an anticonvulsant has been explored (Bryans et al., "Identification of Novel Ligands for the Gabapentin Binding Site on the $\alpha_2\delta$ Subunit of a Calcium Channel and Their Evaluation as Anticonvulsant Agents," *J. Med. Chem.* 41:1838–1845 (1998), which is hereby incorporated by reference). Pregabalin has been shown to possess even higher binding affinity for the $\alpha_2\delta$ subunit of VGCC than gabapentin (Bryans et al., "3-Substituted GABA Analogs with Central Nervous System Activity: A Review," *Med. Res. Rev.* 19:149–177 (1999), which is hereby incorporated by reference).

Other GABA analogs which display binding affinity to the $\alpha_2\delta$ subunit of VGCC include, without limitation, cis-(1S, 3R)-( 1-(aminomethyl)-3-methylcyclohexane)acetic acid, cis-(1R,3S)-(1-(aminomethyl)-3-methylcyclohexane)acetic acid, 1α,3α,5α-(1-aminomethyl)-(3,5-dimethylcyclohexane)acetic acid, (9-(aminomethyl)bicyclo [3.3.1]non-9-yl)acetic acid, and (7-(aminomethyl)bicyclo [2.2.1]hept-7-yl)acetic acid (Bryans et al., "Identification of Novel Ligands for the Gabapentin Binding Site on the $\alpha_2\delta$ Subunit of a Calcium Channel and Their Evaluation as Anticonvulsant Agents," *J. Med. Chem.* 41:1838–1845 (1998); Bryans et al., "3-Substituted GABA Analogs with Central Nervous System Activity: A Review," *Med. Res. Rev.* 19:149–177 (1999), which is hereby incorporated by reference).

The identification of still further compounds, including other GABA analogs, which have a binding affinity for the $\alpha_2\delta$ subunit of VGCC can be determined by performing $\alpha_2\delta$ binding affinity studies as described by Gee et al. ("The Novel Anticonvulsant Drug, Gabapentin (Neurotonin), Binds to the $\alpha_2\delta$ Subunit of a Calcium Channel," *J. Biol. Chem.* 271(10):5768–5776 (1996), which is hereby incorporated by reference).

The present invention requires administration of the compound which binds the $\alpha_2\delta$ subunit of VGCC to a patient under conditions effective to treat either a symptom of hormonal variation or, more specifically, hot flashes (whether hormonally, surgically, drug, or otherwise induced). The effective conditions typically involve administering an amount of such compounds that is effective for the desired treatment. By treating the symptom of hormonal variation, including hot flashes, the present invention encompasses either reducing the number of symptomatic events, reducing the severity of symptomatic events, or both.

Effective amounts of the compound which binds the $\alpha_2\delta$ subunit of VGCC will depend upon the mode of administration, frequency of administration, and the type of pharmaceutical composition used to deliver the compound into a patient. Generally, effective amounts of such compounds will be about 0.01 to about 300 mg/kg·body wt. per day, preferably about 0.1 to about 200 mg/kg·body wt. per day, more preferably about 1 to about 100 mg/kg·body wt. per day. Typical daily doses will be from about 10 to about 5000 mg per day for an average adult patient of normal weight. While individual needs vary, determination of optimal ranges of effective amounts of each compound is within the skill of the art.

The compounds used according to the present invention can be administered alone or as a pharmaceutical composition, which includes the compound(s) and a pharmaceutically-acceptable carrier. The pharmaceutical composition can also include suitable excipients, or stabilizers, and can be in solid or liquid form such as, tablets, capsules, powders, solutions, suspensions, or emulsions. Typically, the composition will contain from about 0.01 to 99 percent, preferably from about 5 to 95 percent of active compound(s), together with the carrier.

The compound which binds the $\alpha_2\delta$ subunit of VGCC, when combined with pharmaceutically or physiologically acceptable carriers, excipients, or stabilizers, whether in solid or liquid form such as, tablets, capsules, powders, solutions, suspensions, or emulsions, can be administered orally, parenterally, subcutaneously, intravenously, intramuscularly, intraperitoneally, by intranasal instillation, by implantation, by intracavitary or intravesical instillation, intraocularly, intraarterially, intralesionally, or by application to mucous membranes, such as, that of the nose, throat, and bronchial tubes (i.e., inhalation).

For most therapeutic purposes, the compound which binds the $\alpha_2\delta$ subunit of VGCC can be administered orally as a solid or as a solution or suspension in liquid form, via injection as a solution or suspension in liquid form, or via inhalation of a nebulized solution or suspension.

The solid unit dosage forms can be of the conventional type. The solid form can be a capsule, such as an ordinary gelatin type containing the compounds of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

For injectable dosages, solutions or suspensions of these materials can be prepared in a physiologically acceptable diluent with a pharmaceutical carrier. Such carriers include sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

For use as aerosols, the compound in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

It is also contemplated that administration of the compound which binds the $\alpha_2\delta$ subunit of VGCC can be carried out in combination with other suitable therapeutic treatments which are useful for treating symptoms of hormonal variation, including hot flashes.

The patient to be treated is any mammalian patient, preferably a human patient. The patient can be either a female patient or a male patient, although the ultimate cause of hot flashes can, of course, be markedly different for both groups of patients. For example, in female patients the hot flash is a primary symptom resulting from menopausal or postmenopausal hormonal variation. However, the hot flash can also be drug-induced by anti-estrogen compounds (e.g., tamoxifen, leuprolide acetate, etc.) or surgically-induced by removal of estrogen-producing tissues (e.g., total abdominal hysterectomy, bilateral salpingo-oophorectomy, etc.). In male patients, the hot flashes typically occur as a side-effect of androgen-dependent therapy for metastatic prostate cancer. They can be either surgically-induced (e.g., bilateral orchiectomy) or drug-induced (e.g., treatment with a gonadotrophin-releasing-hormone agonist, leuprolide acetate, etc.).

It is also believed that compounds which bind the $\alpha_2\delta$ subunit of VGCC can act as antipyretic agents, thereby moderating thermoregulation of a patient. Thus, a further aspect of the present invention relates to a method of treating fever in a patient which is carried out by providing a compound which binds an $\alpha_2\delta$ subunit of a voltage-gated calcium channel and administering the compound to a patient experiencing a fever under conditions effective to treat the fever. By treating the fever, the present invention encompasses reducing or eliminating the fever, either completely or for a limited duration of time (i.e., up to about 24 hours). Preferred compounds include GABA analogs of the type described above, more preferably gabapentin and pregabalin, which can be administered alone or as part of a pharmaceutical composition of the type described above. The treatment can also be carried out in combination with other suitable therapeutic treatments which are useful for controlling or otherwise moderating fever.

It is also believed that compounds which bind the $\alpha_2\delta$ subunit of VGCC can act as anti-emetic agents that are effective for the treatment of nausea and emesis. Nausea and emesis are often induced by stimulation of either the chemoreceptor trigger zone or the emesis (or vomiting) center in the central nervous system. Such stimulation can be caused by afferent stimulation (e.g., tactile pharyngeal impulses, labrynthine disturbances, motion, increased intracranial pressure, pain, distention of viscera or psychologic factors) or blood born emetic substances (e.g., as seen during pregnancy, cancer chemotherapy, uremia, radiation therapy, electrolyte and endocrine disturbances, or the presence of chemical emetic substances). Nausea and vomiting are also common post-operative side effects resulting from the use of anesthetics.

Thus, a further aspect of the present invention relates to a method of treating nausea and emesis in a patient which is carried out by providing a compound which binds an $\alpha_2\delta$ subunit of a voltage-gated calcium channel and administering the compound to a patient experiencing nausea and emesis under conditions effective to treat the nausea and emesis. By treating the nausea and emesis, the present invention encompasses reducing or eliminating the feeling of nausea as well as reducing or eliminating the frequency of emesis, either completely or for a limited duration of time (i.e., up to about 24 hours). Administration of such compounds can occur while a patient is experiencing nausea or emesis or in anticipation of the patient experiencing nausea or emesis. Preferred compounds include GABA analogs of the type described above, more preferably gabapentin and pregabalin, which can be administered alone or as part of a pharmaceutical composition of the type described above. The treatment can also be carried out in combination with other suitable therapeutic treatments which are useful for treating nausea and emesis.

EXAMPLES

The following examples are provided to illustrate embodiments of the present invention but are by no means intended to limit its scope.

Example 1

Administration of Gabapentin to Patients Experiencing Hot Flashes and Other Symptoms of Hormonal Variation Six patients received gabapentin treatments either for purposes of alleviating occurrence of hot flashes or other symptoms of hormonal variation. The relevant data for Patients 1–6 are summarized in Table 1 below. In these six patients, gabapentin treatment is associated with an average 87% reduction in hot flash frequency.

TABLE 1

Summary of Gabapentin Treatment for Patients 1–6

| Patient | Cause of Hot Flashes | Baseline No. Hot Flashes (per 24 h) | Gabapentin Dose (mg · doses) | No. of Days to Respond | Post-Treatment No. Hot Flashes (per 24 h) |
|---|---|---|---|---|---|
| 1 | TAH/BSO | 10–15 | 300 · 3 | 2 | 0 |
| 2 | TAH/BSO | 15–20 | 300 · 3 | 2 | 1 |

TABLE 1-continued

Summary of Gabapentin Treatment for Patients 1–6

| Patient | Cause of Hot Flashes | Baseline No. Hot Flashes (per 24 h) | Gabapentin Dose (mg · doses) | No. of Days to Respond | Post-Treatment No. Hot Flashes (per 24 h) |
|---|---|---|---|---|---|
| 3 | Tamoxifen | 4 | 300 · 3 | 2 | 1 |
| 4 | Leuprolide acetate | 15 | 300 · 1 | 1 | 5 |
| 5 | TAH/BSO | 8 | 200 · 1 | 1 | 0 |
| 6 | TAH/BSO | 40 | 400 · 5 | 3 | 5 |

TAH = total abdominal hysterectomy; BSO = bilateral salpingo-oophorectomy.

Patient 1

Patient 1 is a 52-year-old woman who was status-post total abdominal hysterectomy and bilateral salpingo-oophorectomy in 1993 for uterine fibroids and had been placed on oral estrogen. In 1995, the patient began developing common migraine headaches that responded well to sumatriptan. In September 1998, estrogen was discontinued in an attempt to decrease the frequency of her migraine headaches. One month later, she began to develop typical hot flashes that persisted until she sought neurological consultation the following December. At that time, the patient was having 10 to 15 hot flashes per day and two migraine headaches per week. Gabapentin 300 mg three times a day was started for migraine prophylaxis; the patient did not mention hot flashes on her first visit. Subsequently, the patient reported that her headaches were about the same but, curiously, her hot flashes had completely resolved two days after starting gabapentin treatment. The dose was doubled to maximize migraine prophylaxis.

To assess a causal relationship between gabapentin treatment and the resolution of hot flashes, gabapentin treatment was tapered off over five days. The first day completely off treatment the patient had 11 daytime hot flashes as well as six more overnight, which prevented her from sleeping. Gabapentin 300 mg three times a day was resumed the next morning and the patient has yet to experience another hot flash.

Patient 2

Patient 2 is a 49-year-old woman who was status-post total abdominal hysterectomy/bilateral salpingo-oophorectomy in 1994 secondary to a ruptured fallopian tube. She began having 15–20 hot flashes per day soon afterwards. Hormone replacement therapy was contraindicated secondary to a history of Hepatitis A. The hot flashes often woke Patient 2 from sleep. Patient 2 also described a constant "clammy" feeling over her entire body throughout the day, both during and between hot flashes. Within two days of starting treatment with gabapentin 300 mg three times a day, Patient 2 reported resolution of the "clammy" dysphoric feeling as well as all but one hot flash per day. All nocturnal hot flashes were resolved. Due to persistent somnolence, gabapentin treatment was decreased to 300 mg two times a day without any compromise in efficacy.

Patient 3

Patient 3 is a 62-year-old woman who was placed on tamoxifen for breast cancer. Almost immediately after beginning tamoxifen treatment, she began having three to four hot flashes per day, with the worst hot flash typically occurring after taking an evening dosage of tamoxifen. Hot flashes are a well-known side effect of tamoxifen therapy; tamoxifen acts as an anti-estrogen, creating a chemical menopause. Patient 3 was placed on gabapentin 300 mg three times a day. Two days later, all hot flashes had resolved except for one each day, which occurred shortly after taking tamoxifen. Patient 3 reported that the persistent hot flash event was greatly reduced in severity.

Patient 4

Patient 4 is a 58-year-old man who was previously diagnosed with stage I prostate cancer. Ten days after receiving the standard hormone-altering treatment of 7.5 mg of leuprolide acetate depot injection, Patient 4 began to experience leuprolide acetate's common side effect of hot flashes. He experienced about 15 hot flashes a day, ten of which occurred at night and prevented him from sleeping. Gabapentin treatment of a single 300 mg dose at bedtime completely resolved all nocturnal hot flashes and the consequent daytime sleepiness. Because the patient worked with heavy machinery and preferred not to take any potentially sedating medications during the day, the daytime hot flashes persisted. On several occasions the patient has forgotten to take gabapentin at night, and on each occasion the patient later reported experiencing about ten hot flashes. The patient has never experienced nocturnal hot flashes after taking gabapentin at bedtime.

Patient 5

Patient 5 is a 55-year-old female who was status-post total abdominal hysterectomy/bilateral salpingo-oophorectomy in 1992 for uterine fibroids. She was treated with PREMARIN® for four years and did not experience any hot flashes. In 1996, Patient 5 discontinued PREMARIN® due to side effects of weight gain and persistent menstrual spotting. After cessation of PREMARIN® treatments, Patient 5 experienced about eight nocturnal hot flashes which were associated with nighttime awakenings and consequent daytime sleepiness. Gabapentin treatment of a single 200 mg dose at bedtime was initiated, completely resolving all nocturnal hot flashes and greatly improving the daytime sleepiness.

Patient 6

Patient 6 is a 60-year-old woman who was status-post total abdominal hysterectomy/bilateral salpingo-oophorectomy in 1990 secondary to uterine fibroids. Despite PREMARIN® 0.625 mg per day for seven years, Patient 6 continued to have about 40 hot flashes during the day and six at night. PREMARIN® was discontinued in 1997. Patient 6 received no benefit from gabapentin 300 mg four times a day; however, she did respond to gabapentin 400 mg five times a day. Patient 6 now has about four daytime hot flashes and one nocturnal hot flash.

Example 2

Administration of Gabapentin to Patient Exhibiting Hypothalamic Dysfunction

Patient 7 is a 38-year-old man with a history of childhood tuberculosis meningitis, which resulted in severe mental retardation, seizure disorder, and hypothalamic dysfunction manifest as episodes of hypothermia occurring about once every 2 years. Gabapentin was added to his anticonvulsant regimen of phenobarbital and carbamazepine for seizure control. Over the following 6 months, the patient had 23 episodes of hypothermia, often with concomitant unresponsiveness. The lowest recorded temperature was 95.0° F., with the average hypothermic temperature being 96.7° F. All temperatures were recorded rectally. Blood sugars and thyroid function tests remained normal throughout these events. After six months of gabapentin treatment, no further gabapentin was administered. The patient's next hypothermic episode was about one and a half years later. Patient 7 has experienced two other hypothermic episodes, but the frequency of these episodes was substantially less than during the six months of treatment. No other medication in the patient's history has been reported to increase the frequency of his hypothermic episodes.

Patient 7 experienced an approximately 100-fold increase in frequency of hypothermic episodes during six months of gabapentin treatment. Once gabapentin administration was discontinued, the hypothermic episodes returned substantially to their baseline frequency.

DISCUSSION

Although gabapentin's actual mechanism of action is unknown, unique binding sites for [$^3$H]-gabapentin have been shown to concentrate in the cortex, hippocampus, basal ganglia, and cerebellum of male rat brain (Thurlow et al., "Comparison of the Autoradiographic Binding Distribution of [$^3$H]-Gabapentin with Excitatory Amino Acid Receptor and Amino Acid Uptake Site Distributions in Rat Brain," *Br. J. Pharmacol.*, 118:457–465 (1996), which is hereby incorporated by reference). These binding sites are now known to be located on the $\alpha_2\delta$ subunit of VGCC (Gee et al., "The Novel Anticonvulsant Drug, Gabapentin (Neurontin), Binds to the Alpha 2 Delta Subunit of a Calcium Channel," *J. Biol. Chem.*, 271:5768–5776 (1996), which is hereby incorporated by reference). Hypothalamic calcium channel activity has been implicated as a mediator of temperature regulation (Pillai et al., "Activation of Dihydropyridine Receptors Differentially Regulates Temperature Responses in Rat," *Pharmacol. Biochem. Behav.*, 25:549–554 (1986), which is hereby incorporated by reference). N-type VGCC are concentrated in male and female rabbit brain cortex, basal ganglia, hippocampus, and ventromedial hypothalamus (VMH) (Whorlow et al., "Distribution of N-Type Ca2+ Channel Binding Sites in Rabbit Brain Following Central Administration of Omega-Conotoxin GVIA," *Eur. J. Pharmacol.*, 315:11–18 (1996), which is hereby incorporated by reference). Inhibition of rat VMH in vivo causes hypothermia (Shiraishi et al., "Hypothermia Following Injection of 2-deoxy-D-glucose Into Selected Hypothalamic Sites," *Am. J. Physiol.*, 239:R265-R269 (1980), which is hereby incorporated by reference). The VMH also harbors the largest substance-P projection to a principal hypothalamic cooling center, the medial preoptic area (Yamano et al., "A Substance P-Containing Pathway from the Hypothalamic Ventromedial Nucleus to the Medial Preoptic Area of the Rat: An Immunohistochemical Analysis," *Neuroscience*, 18:395–402 (1986), which is hereby incorporated by reference). Without being bound by theory, it is believed that the VMH may represent gabapentin's site of action in the treatment of hot flashes and the exacerbation of hypothermic episodes in Patient 7.

Although the invention has been described in detail for the purposes of illustration, it is understood that such detail is solely for that purpose, and variations can be made therein by those skilled in the art without departing from the spirit and scope of the invention which is defined by the following claims.

What is claimed:

1. A method of treating hot flashes in a patient comprising:
   providing a compound which binds an $\alpha_2\delta$ subunit of a voltage-gated calcium channel and
   administering the compound to a patient experiencing hot flashes under conditions effective to treat the hot flashes.

2. The method according to claim 1, wherein the compound is a γ-aminobutyric acid analog or salt thereof.

3. The method according to claim 2, wherein the γ-aminobutyric acid analog is gabapentin or pregabalin.

4. The method according to claim 3, wherein the γ-aminobutyric acid analog is gabapentin.

5. The method according to claim 2, wherein the γ-aminobutyric acid analog is administered in an amount of about 10 to about 5000 mg per day.

6. The method according to claim 1, wherein the patient is a female patient.

7. The method according to claim 6, wherein the female patient is postmenopausal.

8. The method according to claim 7, wherein menopause is drug induced, surgically induced, or naturally-occurring.

9. The method according to claim 8, wherein menopause is drug induced.

10. The method according to claim 9, wherein the drug is an anti-estrogen compound.

11. The method according to claim 10, wherein the anti-estrogen compound is tamoxifen.

12. The method according to claim 1, wherein the patient is a male patient.

13. The method according to claim 12, wherein the male patient experiences drug induced hot flashes.

14. The method according to claim 13, wherein the drug is an anti-androgen compound.

15. The method according to claim 14, wherein the anti-androgen compound is leuprolide acetate.

16. The method according to claim 1, wherein said administration is carried out orally, parenterally, subcutaneously, intravenously, intramuscularly, intraperitoneally, by intranasal instillation, by implantation, by intracavitary or intravesical instillation, intraocularly, intraarterially, intralesionally, or by application to mucous membranes.

17. The method according to claim 1, wherein the compound is present in a pharmaceutical composition comprising the compound and a pharmaceutically-acceptable carrier.

18. The method according to claim 17, wherein the pharmaceutical composition is in a liquid or solid dosage form.

19. A method for treating a symptom of hormonal variation in a patient comprising:
    providing a compound which binds an $\alpha_2\delta$ subunit of a voltage-gated calcium channel and
    administering the compound to a patient experiencing a symptom of hormonal variation under conditions effective to treat the symptom of hormonal variation.

20. The method according to claim 19, wherein the patient is a postmenopausal female patient.

21. The method according to claim 20, wherein menopause is drug induced, surgically induced, or natural.

22. The method according to claim 19, wherein the compound is a γ-aminobutyric acid analog.

23. The method according to claim 22, wherein the γ-aminobutyric acid analog is gabapentin or pregabalin.

24. The method according to claim 23, wherein the γ-aminobutyric acid analog is gabapentin.

25. The method according to claim 19, wherein the patient is a male patient undergoing androgen-dependent therapy.

26. The method according to claim 25, wherein the androgen-dependent therapy is surgical or drug therapy.

27. The method according to claim 19, wherein said administering is carried out orally, parenterally, subcutaneously, intravenously, intramuscularly, intraperitoneally, by intranasal instillation, by implantation, by intracavitary or intravesical instillation, intraocularly, intraarterially, intralesionally, or by application to mucous membranes.

28. The method according to claim 19, wherein the compound is present in a pharmaceutical composition comprising the compound and a pharmaceutically-acceptable carrier.

29. The method according to claim 28, wherein the pharmaceutical composition is in a liquid or solid dosage form.

30. A method of treating fever in a patient comprising:
providing a compound which binds an $\alpha_2\delta$ subunit of a voltage-gated calcium channel and
administering the compound to a patient experiencing a fever under conditions effective to treat the fever.

31. The method according to claim 30, wherein the compound is a γ-aminobutyric acid analog.

32. The method according to claim 31, wherein the γ-aminobutyric acid analog is gabapentin or pregabalin.

33. The method according to claim 32, wherein the γ-aminobutyric acid analog is gabapentin.

34. The method according to claim 30, wherein said administering is carried out orally, parenterally, subcutaneously, intravenously, intramuscularly, intraperitoneally, by intranasal instillation, by implantation, by intracavitary or intravesical instillation, intraocularly, intraarterially, intralesionally, or by application to mucous membranes.

35. The method according to claim 30, wherein the compound is present in a pharmaceutical composition comprising the compound and a pharmaceutically acceptable carrier.

36. The method according to claim 35, wherein the pharmaceutical composition is in a liquid or solid dosage form.

* * * * *